United States Patent [19]

Whalen et al.

[11] Patent Number: 4,613,503

[45] Date of Patent: Sep. 23, 1986

[54] ANTIBIOTIC A26201-1 AND ANTIBIOTIC A26201-2 PRODUCED BY A NOVEL STRAIN OF ACTINOPLANES

[75] Inventors: Joseph W. Whalen; Gregory L. Swartz; Lisa J. Rheaume; Karen M. McCoy, all of Midland, Mich.

[73] Assignee: The Dow Chemical Company, Midland, Mich.

[21] Appl. No.: 659,912

[22] Filed: Oct. 11, 1984

[51] Int. Cl.$^4$ .......................... A61K 35/74; C12P 1/06
[52] U.S. Cl. ................................ 424/117; 424/124; 435/169
[58] Field of Search ................ 424/117, 124; 435/169

[56] References Cited

U.S. PATENT DOCUMENTS

| | | | |
|---|---|---|---|
| 3,952,095 | 4/1976 | Hamill et al. | 424/118 |
| 3,968,204 | 7/1976 | Hamill et al. | 424/121 |
| 4,035,481 | 7/1977 | Berg et al. | 424/122 |
| 4,064,233 | 12/1977 | Hamill et al. | 424/118 |
| 4,083,963 | 4/1978 | Celmer et al. | 424/117 |
| 4,115,552 | 9/1978 | Hamill et al. | 424/118 |
| 4,141,907 | 2/1979 | Nakatsukasa et al. | 260/345.7 R |
| 4,148,882 | 4/1979 | Celmer et al. | 424/122 |
| 4,150,152 | 4/1979 | Celmer et al. | 424/122 |
| 4,174,390 | 11/1979 | Hamill et al. | 424/117 |
| 4,239,751 | 12/1980 | Coronelli et al. | 424/118 |
| 4,303,646 | 12/1981 | Cavalleri et al. | 424/118 |
| 4,322,406 | 3/1982 | Debono et al. | 424/118 |
| 4,375,513 | 3/1983 | Debono et al. | 435/169 |

OTHER PUBLICATIONS

J. Antibiotics, 29, 505–515 (1976).

*Primary Examiner*—Jerome D. Goldberg
*Attorney, Agent, or Firm*—Thomas R. Savitsky; Kenneth L. Loertscher

[57] ABSTRACT

Antibiotic A26201-1 and antibiotic A26201-2 are produced by the novel microorganism, Actinoplanes species A26201 (ATCC 39573), under aqueous aerobic fermentation conditions. The antibiotics are useful for inhibiting bacteria, particularly gram positive bacteria, and are also useful for promoting the growth of monogastric and ruminant animals.

15 Claims, 7 Drawing Figures

ANTIBIOTIC A26201-1 AND ANTIBIOTIC A26201-2 PRODUCED BY A NOVEL STRAIN OF ACTINOPLANES

BACKGROUND OF THE INVENTION

Substances active against microorganisms have many beneficial uses. These uses are in fields such as human health care, veterinary science, and animal husbandry. Antimicrobial agents can have many desirable effects such as preventing or curing disease and promoting the growth of animals.

New antimicrobial agents are needed for several reasons; these include intolerance of the subject to be treated to known antimicrobials, and the development of strains resistant to known antimicrobials. Therefore characterization of any previously known microorganisms which produce new antimicrobial agents is highly desirable.

SUMMARY OF THE INVENTION

The present invention is directed to novel biologically active substances produced by the fermentation of the novel microorganism Actinoplanes species A26201 and the process of production thereof. Although this organism is a member of the genus Actinoplanes, it cannot be placed into any of the previously known species and therefore represents a previously unknown species of Actinoplanes. Processes using mutant organisms derived from the species disclosed herein are considered to be within the scope of this invention. Mutant organisms of Actinoplanes species A26201 may be obtained by chemical or physical techniques, or by other techniques appreciated in the art. A subculture of Actinoplanes species A26201 has been made part of the permanent collection of the American Type Culture Collection, 12301 Parklawn Drive, Rockville, Md., where it is assigned the accession No. 39573.

The novel biologically active substances of this invention which are produced by the fermentation of Actinoplanes species A26201 have antimicrobial and/or growth promotion activities. For simplicity of discussion, these substances will be referred to generally as "antibiotics." The term "crude broth material" refers to an unpurified mixture of antibiotics consisting of a dried or aqueous aliquot of culture medium having antibiotic and/or growth promotion activity after fermentation by Actinoplanes species A26201. The term "antibiotic A26201" refers to a partially purified mixture of antibiotics derived from the crude broth material. A step-gradient elution system using acetonitrile in water on a reverse phase preparative liquid chromatography system was used to obtain this partially purified material which includes the two novel active components. The terms "antibiotic A26201-1" and "antibiotic A26201-2" refer to two distinct, purified, active components contained in the crude broth material and in antibiotic A26201. The term "appropriate microorganism" refers to a microorganism capable of producing antibiotic A26201-1 and/or antibiotic A26201-2 such as Actinoplanes species A26201 or any other microorganism such as mutants of Actinoplanes species A26201 which is capable of producing at least one of said antibiotics.

The antibiotics of this invention are differentiated from known substances by their chemical and physical properties as well as their range of antibiotic activity. The term "inhibition" or "inhibiting" refers to antimicrobial activity such as the suppression, control, kill, stasis, or destruction of microorganisms, or any interference with the growth of microorganisms which results in a slower growth rate. The term "effective amount" refers to that amount of biologically active substance sufficient to result in inhibition of microorganisms.

The present invention is also directed to a method of producing the novel antibiotics of this invention which comprises growing Actinoplanes species A26201 in a suitable nutrient medium and recovering the antibiotics therefrom. The antibiotics of this invention are useful as antimicrobial agents and/or as growth promoting agents in monogastric and ruminant animals. The term "animals" refers to those animals in which it is desirable to increase the growth rate and/or feed conversion efficiency; the term "monogastric animals" refers to those animals without a developed rumen function in which it is desirable to increase the growth rate and/or the feed conversion efficiency such as swine or poultry; the term "ruminant animals" refers to those animals with a developed rumen function in which it is desirable to increase the growth rate and/or feed conversion efficiency such as cattle or sheep; the term "growth promoting amount" refers to that amount of antibiotic or antibiotics sufficient to increase the growth rate and-/or feed conversion efficiency of the treated animals without resulting in any significant adverse side effects; the term "standard animal feed" refers to customary animal feed for monogastric and/or ruminant animals as commonly known in the art.

DETAILED DESCRIPTION OF THE INVENTION

Figure 1:
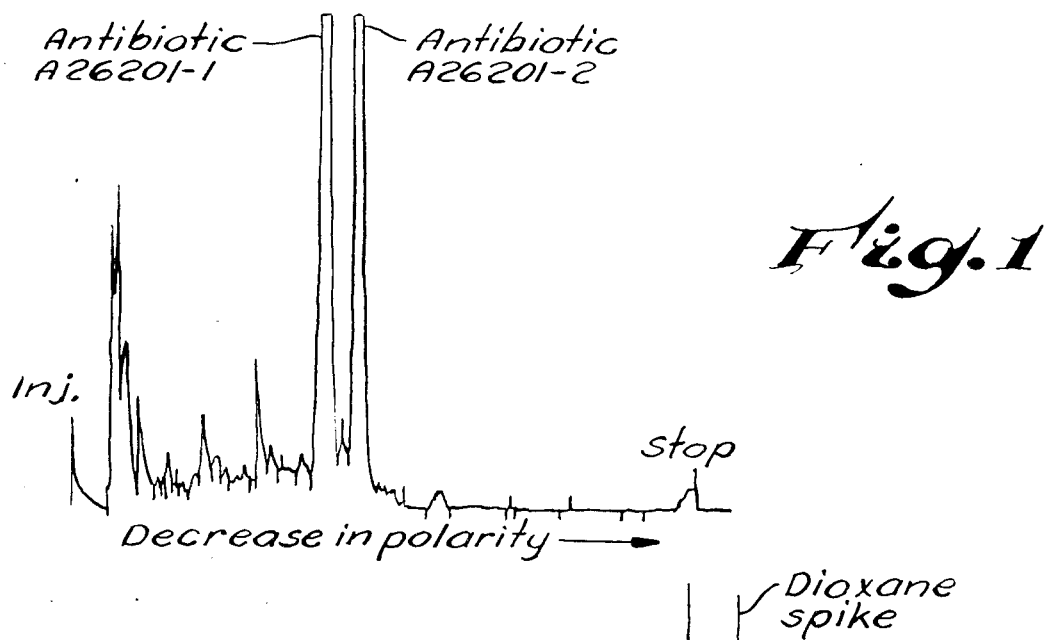
FIG. 1—Reverse phase high performance liquid chromatograph illustrating the separation of the fractions containing antibiotic A26201-1 and antibiotic A26201-2. Inj. refers to where the sample was injected.

The genus Actinoplanes is characterized in "Bergey's Manual of Determinative Bacteriology," 8th edition, Williams & Wilkins, 1974, as having sporangia which are 3 to 20 by 6 to 30 micrometers ($\mu$m) in size. The sporangia can be spherical, subspherical, cylindrical with rounded ends, or very irregular. The spores are globose to subglobose, 1 to 1.5 $\mu$m in diameter, occur in coils, nearly straight chains, or are irregularly arranged in sporangia. The spores are also motile by a tuft of polar flagella 2 to 6 $\mu$m in length. The hyphae are 0.2 to 2.6 $\mu$m in diameter, branched, irregularly coiled, twisted or straight with few septa. Vertical pallisade hyphae are formed on certain agars; aerial mycelia are scanty, except in *A. armeniacus*. Most species are brilliantly colored on peptone Czapek and certain other agars; colors are orange, red, yellow, violet and purple. Some strains form diffusible pigments which color the agar blue, red, yellow, brownish or greenish. No organic growth factors are required H$_2$S is produced by some species. All members of the genus are strict aerobes. Temperature range for growth is 18° C. to 35° C. The organisms occur on a wide variety of plant material, less often on parts of dead animals such as hair, hoofs, snake skin. The Guanine+Cytosine content of the DNA (of two species studied) ranges from 72.1 to 72.6 mole %.

The novel microorganism, Actinoplanes species A26201, was isolated from a soil sample. This species grows well on a variety of nutrient media resulting in characteristic macroscopic morphology. For example, after 5 to 7 days incubation on oatmeal agar, the colonies are about 5 to 6 millimeters (mm) in diameter and have an undulate surface. A sparse mycelium and orange pigment are also produced. On some other media, abundant aerial mycelia are produced.

When grown on most agar media, Actinoplanes species A26201 produces sporangia; these sporangia are frequently seen on the central portion of individual colonies. The sporangia are spherical to oval in shape, have regular contours and a diameter ranging from about 15 to 25 μm. Sporangiospores are straight, about 15 μm long with a diameter of about 2 μm. The spores are highly motile and are spherical to oval with a diameter of about 1.5 to 2 μm.

After fermentation of Actinoplanes species A26201, antibiotic A26201-1 and antibiotic A26201-2 are found in the fermentation broth. The crude broth material can be partially purified by standard purification procedures such as various chromatographic techniques. The preferred method is preparative reverse phase liquid chromatography using a step gradient which yields antibiotic A26201. Antibiotic A26201 can then be resolved into antibiotic A26201-1 and antibiotic A26201-2 by separation techniques such as a semipreparative reverse phase high performance liquid chromatography system. The individual antibiotics are then further purified by removing any buffers and solvents required in the separation procedure. The purified antibiotics can then be lyophilyzed.

Antibiotic A26201 contains amino acids and inhibits cell wall synthesis. These characteristics are shared by known antibiotics produced by other Actinoplanes species, see U.S. Pat. Nos. 4,239,751; 4,303,646; 4,375,513; and *J. Antibiotics*, 29, 501–506, 511–515 (1976). The antibiotics produced by Actinoplanes species A26201 most closely resemble gardimycin which is produced by either *Actinoplanes garbadinensis* or *Actinoplanes liguriae*. However, antibiotic A26201-1, antibiotic A26201-2, and gardimycin can be differentiated by their respective physical and chemical characteristics. In addition, Actinoplanes species A26201, *Actinoplanes garbadinensis*, and *Actinoplanes liguriae* can be differentiated by their respective cultural, biochemical, and physiological characteristics, as well as their ability to use various carbon sources.

In the preparation of the novel antibiotics of this invention, Actinoplanes species A26201 is cultivated under aerobic conditions in a nutrient medium suitable for its growth until the antibiotics are produced by said microorganism in said culture medium. For example, the maintenance, seed, and fermentation media described herein are inoculated and incubated for about 2 to 14 days, 5 to 7 days being preferred, at a temperature of about 20° C. to 35° C., 28° C. to 30° C. being preferred. Incubation with agitation is preferred with aqueous media. The pH of the media described herein prior to inoculation is about 6 to 8, with 6.8 to 7.3 being preferred.

Actinoplanes species A26201 is capable of using at least one of several conventional nitrogen sources in a concentration from about 0.1% to 10% of medium such as casamino acids, HY-SOY ®, N-Z amine, Brain Heart infusion, Trypticase Soy, Peptone, and Casitone. The carbohydrate source can be at least one of several common carbohydrates such as glucose, starch, mannose, fructose, glycerol, lactose, sucrose and maltose, with fructose and sucrose being preferred at a concentration from about 0.1% to 10% of medium. Essential trace minerals and trace elements can also be added to the medium. Frequently, such trace minerals and elements occur as impurities in other constituents of the medium in amounts sufficient to meet the growth requirements of the organism.

Addition of at least one amino acid such as tryptophan or valine to the media further stimulates fermentation activity.

To determine antibiotic activity an assay using a susceptible microorganism such as *Clostridium perfringens* or *Sarcina lutea* can be employed.

The antibiotics of the present invention can be used in a wide variety of applications in which inhibition of microorganisms is desired. The antibiotics are active against pathogenic and non-pathogenic bacteria which may be resistant to widely used known antibiotics. Because of this activity, the antibiotics of the present invention can be used as therapeutic agents either alone or in combination with pharmaceutically-acceptable carriers.

The antibiotics of the present invention or combinations containing the same can also be used as disinfectants, for example, to disinfect objects and instruments. The novel antibiotics can be used as antibacterial agents, for example, by contacting bacterial pests or their habitat with effective amounts sufficient to obtain inhibition of many organisms. The antibiotics of this invention can be incorporated into various products susceptible to microbial degradation in order to prevent such degradation of the products by the microorganisms.

The novel antibiotics can also be used as growth promoting agents in animals. In monogastric or ruminant animals, the antibiotics can be administered to said animals by common means appreciated by one skilled in the art (for example, see the methods taught in U.S. Pat. Nos. 4,185,091; 4,209,518; 4,333,923; incorporated herein by reference). In monogastric animals, the antibiotics can be administered in combinations with standard animal feed wherein the concentration of said antibiotic or antibiotics is about 5 to 25 parts per million (ppm) of the ultimate feed composition. The novel antibiotics can also be administered to ruminant animals by means of combinations with standard animal feed wherein the concentration of said antibiotic or antibiotics is about 2 to about 25 ppm of the ultimate feed composition.

The present invention is further illustrated by the following examples; however, these examples are not to be interpreted as a limitation upon the scope of the present invention.

EXAMPLE 1

A new species of Actinoplanes, referred to herein as Actinoplanes species A26201 (ATCC 39573) has been isolated. This species is capable of producing the active substances, antibiotic A26201-1 and antibiotic A26201-2. The cultural characteristics on different media of Actinoplanes species A26201 as well as those of two related species of Actinoplanes (*A. garbadinensis* and *A. liguriae*) are shown in Table 1. The cultural characteristics were determined after 5 to 7 days incubation at 28° to 30° C.

The alpha numeric codes in Table 1 refer to standard color references as described by Maery and Paul (Maery, A. and Paul, M., A Dictionary of Color, 2nd ed., (1950) McGraw-Hill, New York).

TABLE 1
Cultural Characteristics of Some *Actinoplanes* Species

| Culture Medium | Cultural Characteristics |
|---|---|
| | Species A26201 |
| Bennett's Agar | Moderate growth with worty surface, orange surface light orange. |
| Czapek Glucose Agar | Moderate growth with raised worty surface, orange 10/G/9. |
| Czapek Sucrose Agar | Moderate growth with raised worty surface, mycelia present 9/A/2. |
| Glucose Asparagine Agar | Heavy rounded smooth orange growth, sparse mycelia, sparse sporangia. |
| Potato Agar | Sparse orange round smooth colonies. |
| Nutrient Agar | Sparse orange growth 10/G/6, few sporangia, amber diffusible pigment 13/E/4. |
| Peptone Glucose Agar | Moderate orange worty growth 10/G/9, Brown Diffusible pigment 13/E/8. |
| Potato Plug | Poor thin growth with wrinkled surface, light orange 10/A/3. |
| Yeast Extract Malt Agar | Heavy thick wrinkled growth, orange, sporangia, mycelia 9/A/2. |
| Oatmeal Agar 20% | Sparse undulate growth, orange, widely spread sparse mycelia 9/A/2. |
| Inorganic Salts Agar | Moderate thin layer growth, light orange 10/E/4. |
| Glycerol Asparagine Agar | Round raised smooth growth, orange, pink aerial mycelia 9/A/2. |
| Peptone-yeast Extract Iron Agar | Very light growth, orange 10/G/9. Purple soluble pigment 56/E/4. |
| Tyrosine Agar | Heavy growth, raised smooth round colonies orange 10/G/9, sparse mycelia 9/A/2. |
| Skim Milk Agar | Moderate smooth round growth, orange 10/G/9. Sparse sporangia 9/A/2, brown soluble pigment 13/E/8. |
| Agar | no growth. |
| | *A. garbadinensis* |
| Bennett's Agar | Abundant growth, wrinkled surface, light orange. |
| Czapek Glucose Agar | Poor growth, smooth surface, light orange. Traces of rudimentary aerial mycelium. |
| Czapek Sucrose Agar | Poor growth, crusty surface, light orange. |
| Glucose Asparagine Agar | Abundant growth, crusty surface, deep orange. |
| Potato Agar | Abundant growth, wrinkled surface, orange to light brown. Traces of rudimentary aerial mycellium. |
| Nutrient Agar | Moderate growth, crusty surface, orange to light brown. |
| Peptone Glucose Agar | Very scanty growth, smooth surface, hyaline. |
| Potato Plug | Scanty growth, wrinkled surface, orange. |
| Yeast Extract Malt Agar | Abundant growth, wrinkled surface, amber. |
| Oatmeal Agar 20% | Moderate growth, smooth, opaque, cream to orange at edges. |
| Inorganic Salts Agar | Moderate growth, smooth surface, orange. |
| Glycerol Asparagine Agar | Moderate growth, smooth surface, orange. |
| Peptone-yeast Extract Iron Agar | Scanty growth, rough surface, dark brown with brown pigment. |
| Tyrosine Agar | Abundant growth, crusty surface, coffee-colored. Faintly brown pigment. |
| Skim Milk Agar | Abundant growth, wrinkled surface, deep orange. |
| Agar | Very scanty growth, thin and smooth, hyaline. |
| | *A. liguriae* |
| Bennett's Agar | Abundant growth with crusty surface. |
| Czapek Glucose Agar | Abundant growth with smooth and thin surface, orange. Abundant production of sporangia. |
| Czapek Sucrose Agar | Scarce growth, light orange. Moderate production of sporangia. |
| Glucose Asparagine Agar | Abundant growth with smooth surface, orange. Some sporangia. |
| Potato Agar | Abundant growth, with smooth surface, amber. |
| Nutrient Agar | Abundant growth with smooth surface, orange. |
| Peptone Glucose Agar | Abundant growth, with wrinkled surface, deep orange. |
| Potato Plug | Scanty growth, wrinkled, light orange. |
| Yeast Extract Malt Agar | Abundant growth, slightly wrinkled, light orange to light amber. |
| Oatmeal Agar 20% | Abundant growth, with smooth and thin surface, light orange. Some sporangia, light yellow soluble pigment. |
| Inorganic Salts Agar | Abundant growth with smooth surface, orange. Some sporangia. Canary yellow soluble pigment. |
| Glycerol Asparagine Agar | Abundant growth with smooth surface, light orange. Abundant production of pigment. Canary yellow soluble pigment. |
| Peptone-yeast Extract Iron Agar | Moderate growth with smooth surface, orange. |
| Tyrosine Agar | Abundant growth with smooth surface, rose amber. Good production of sporangia. Rose amber soluble pigment. |
| Skim Milk Agar | Abundant growth with slightly crusty surface, deep orange. Yellow soluble pigment. |
| Agar | Very scanty growth thin and smooth. Colorless. |

Table 2 compares the ability of Actinoplanes species A26201, *Actinoplanes garbadinensis* and *Actinoplanes liguriae* to use various carbohydrate sources. Conventional methods were used for the determination. Final concentration of each carbohydrate was 1% of the total medium.

TABLE 2
Carbohydrate Utilization Pattern

| Carbon Source | A. species A26201 | A. liguriae | A. garbadinensis |
|---|---|---|---|
| $C_5$ arabinose | + | + | + |
| xylose | + | + | + |
| $C_6$ glucose | + | + | + |
| fructose | + | + | + |
| mannose | + | + | + |
| mannitol | + | − | + |
| inositol | +/− | + | − |
| rhamnose | + | + | + |
| $(C_6)_2$ sucrose | + | − | + |
| lactose | +/− | − | + |
| $(C_6)_3$ raffinose | +/− | − | |

TABLE 2-continued

| | Carbohydrate Utilization Pattern | | |
|---|---|---|---|
| Carbon Source | A. species A26201 | A. liguriae | A. garbadinensis |
| $(C_6)_n$ cellulose | − | − | − |
| starch | + | + | + |

+ = utilization
+/− = weak utilization
− = no utilization

Table 3 compares biochemical and physiological properties of Actinoplanes species A26201, *Actinoplanes liguriae* and *Actinoplanes garbadinensis*. All biochemical and physiological properties were either performed on petri plates according to conventional methods, or an API strips (Analytab Products, Planview, N.Y.).

TABLE 3

| | Biochemical and Physiological Properties | | |
|---|---|---|---|
| Property | A. species A26201 | A. liguriae | A. garbadinensis |
| indole production | − | − | − |
| starch hydrolysis | ++ | ++ | ++ |
| urease activity | +/− | +/− | + |
| gelatin liquefaction | +/− | − | ++ |
| esculin hydrolysis | ++ | − | +/− |
| catalase | +/− | ++ | ++ |
| hippurate hydrolysis | − | +/− | − |
| leucine aminopeptidase | +/− | + | + |
| serine aminopeptidase | + | + | + |
| pyroglutamic aminopeptidase | + | + | + |
| arginine aminopeptidase | + | + | + |
| β-galactosidase | + | + | + |
| β-glucosidase | + | + | + |
| alkaline phosphatase | + | + | + |
| arginine dehydrogenase | +/− | + | + |
| β-glucosaminidase | + | + | + |
| indoxale acetate hydrolysis | + | + | + |

− = negative
+/− = weak positive
+ = positive
++ = strong positive

From the microscopic and macroscopic morphology, strain A26201 is recognized as a member of the genus Actinoplanes. Other data indicate that Actinoplanes species A26201 differs from closely related species such as *A. liguriae* and *A. garbadinensis* and represents a new species of Actinoplanes. As seen in Table 3, Actinoplanes species A26201 from *A. liguriae* with regard to gelatin liquefaction, esculin hydrolysis, hippurate hydrolysis, catalase, leucine aminopeptidase and arginine dehydrogenase activities, while Actinoplanes species A26201 differs from *A. garbadinensis* with regard to urease activity, gelatin liquefaction, esculin hydrolysis, catalase, leucine aminopeptidase and arginine dehydrogenase activities. Table 2 shows that Actinoplanes species A26201 differs from *Actinoplanes liguriae* with regard to utilization of mannitol, inositol, sucrose, lactose, and raffinose, while Actinoplanes species A26201 differs from *Actinoplanes garbadinensis* with regard to utilization of inositol, lactose and raffinose. All three strains are sufficiently dissimilar to warrant classification as three separate species.

EXAMPLE 2

For growth of seed cultures and fermentation cultures, the media E25, modified E25, E10, and CAAYE, shown in Table 4, are suitable. Oatmeal agar, also shown in Table 4, is suitable for culture maintenance.

TABLE 4

| | Composition of Media | | | | |
|---|---|---|---|---|---|
| Component | E25 | Modified E25 | E10 | Oatmeal Agar | CAAYE |
| Glucose | 25 g | — | 10 g | — | 10 g |
| Fructose | — | 25 g | — | — | — |
| Beef Extract | 4 g | 4 g | 4 g | — | — |
| Yeast Extract | 1.0 g | 1.0 g | 1.0 g | — | 4 g |
| NaCl | 2.5 g | 2.5 g | 2.5 g | — | — |
| Peptone | 4 g | 4 g | 4 g | — | — |
| Soybean Meal | 10 g | 10 g | 10 g | — | — |
| $CaCO_3$ | 5 g | 5 g | 5 g | — | — |
| Casamino Acids | — | — | — | — | 5 g |
| Difco Oatmeal | — | — | — | 200 g | — |
| Tap Water | 1000 ml | 1000 ml | 1000 ml | 1000 ml | — |
| Distilled Water | — | — | — | — | 1000 ml |
| Agar | — | — | — | 20 g | — |

EXAMPLE 3

A pure culture of Actinoplanes species A26201 was inoculated onto an oatmeal agar slant and incubated at 28° C. to 30° C. for seven days. This maintenance culture was then used to inoculate 100 ml of sterile modified E25 seed medium in a sterile 500 ml capped culture flask. The seed culture was then incubated at 28° C. to 30° C. for two days on a shaking apparatus at about 200 revolutions per minute (RPM). After fermentation, 10 ml of the seed culture medium was used to inoculate 100 ml of sterile modified E25 fermentation medium in a sterile 500 ml capped culture flask. The resulting fermentation culture was incubated at 28° C. to 30° C. for six days on a shaking apparatus at about 200 RPM's. The pH of the modified E25 seed and fermentation media was about 7 prior to inoculation.

The antimicrobial activity of the fermentation broth was determined by use of a paper-disc agar diffusion system. A portion of the fermentation broth produced by species A26201 in E25 medium was stored frozen at −20° C. and used as a standard in all assays. One microliter (μl) of the antibiotic standard was arbitrarily designated to contain one unit of activity. Various dilutions of the standard were made and 20 μl of each dilution was pipetted onto paper discs. The discs were then placed onto preseeded *C. perfringens* plates. The discs were allowed to dry and the antibiotic allowed to diffuse into the agar. The plates were then incubated for 16 to 24 hours at 37° C. anaerobically, after which, the size of the zone was measured. A standard curve was constructed and experimental data compared to the standard curve to determine the concentration of antibiotics.

EXAMPLE 4

The active components (i.e., antibiotic A26201-1 and antibiotic A26201-2) were isolated from the crude broth material by a step-gradient elution system using acetonitrile ($CH_3CN$) in water, on a reverse phase preparative liquid chromatography system (Waters Prep-500 LC System). The crude broth material, after filtration was adjusted to pH 7 and loaded onto the column then rinsed with 20% acetonitrile in water, followed by elution of the active components in 30% acetonitrile in water (this preparation of the active components in 30% acetonitrile in water is antibiotic A26201). No further elution of the active components occurred using 100% acetonitrile. The active components in 30% acetonitrile were separated from each other using 34% $CH_3CN$ in a triethylamine-phosphate buffer (0.25N $H_3PO_4$ adjusted to pH 3.5 using triethylamine) on a semi-preparative reverse phase HPLC system (Zorbax ® (Dupont) reverse phase ($C_{18}$) ODS HPLC column (9.4 mm inside diameter × 250 mm length)) giving two active fractions; one fraction containing antibiotic A26201-1 and the other fraction containing antibiotic A26201-2 (see FIG. 1).

The fractions containing antibiotic A26201-1 and antibiotic A26201-2 obtained as described above were each respectively treated as follows: The active fraction was slowly loaded onto a reverse phase (Zorbax ®, ODS) column and the column rinsed with $H_2O$, then washed with low concentrations of acetonitrile in $H_2O$ (5% $CH_3CN$, 10% $CH_3CN$, 15% $CH_3CN$, and 20% $CH_3CN$) over a period of approximately 1 hour. The purified component was eluted with 35% $CH_3CN$ in $H_2O$. After removal of the solvent ($CH_3CN$) by rotary-vaporization, the solution was lyophilized 48 hours to give the purified antibiotic, in each case, as a fine white powder.

EXAMPLE 5

Characterization of antibiotic A26201-1 and antibiotic A26201-2

(A) High Performance Liquid Chromatography (HPLC) Determination

The filtered crude broth material was injected onto a C-18 reverse phase analytical HPLC column with an isocratic elution using 30% ultraviolet (uv) grade acetonitrile/70% 32 mM ammonium formate in water. The flow rate was 2 milliliters/minute (min) and uv detection was at 220 nanometers. The retention time for antibiotic A26201-1 was 5.11 min and the retention time for antibiotic A26201-2 was 737 min.

(B) Ultraviolet Absorption Spectra

Figure 3:
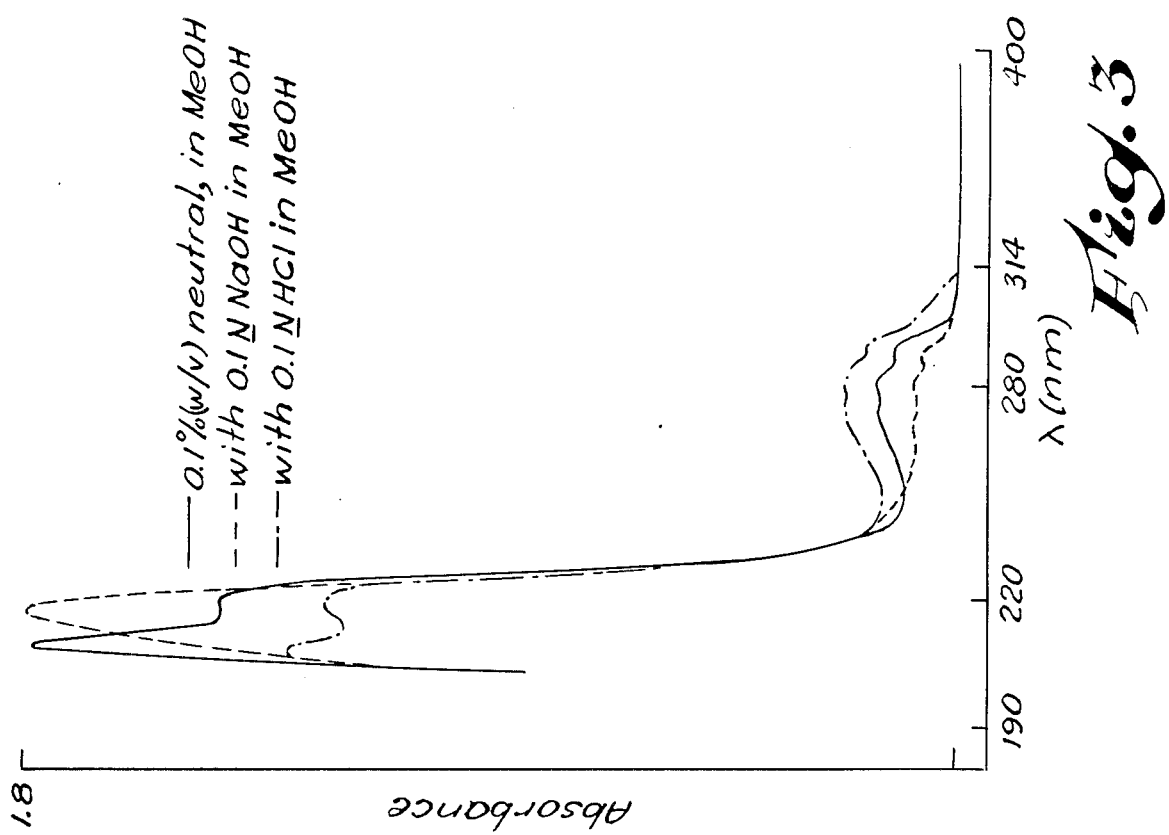
FIG. 3—Ultraviolet absorption spectrum of antibiotic A26201-2. The ordinate limit for the dashed line representing 0.1N NaOH in methyl alcohol (MeOH) was changed to 2.0 to accommodate the new λ maximum at 218.6 nanometers.
Figure 2:
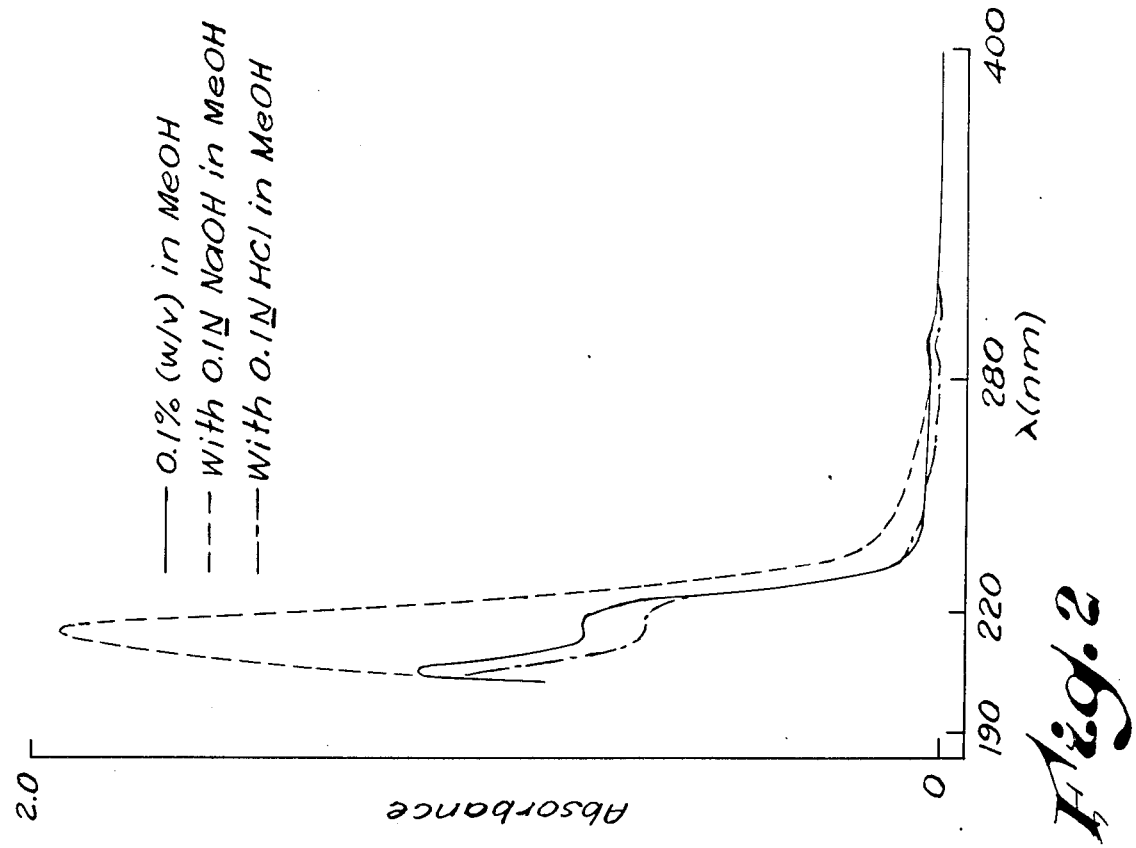
FIG. 2—Ultraviolet absorption spectrum of antibiotic A26201-1.

The ultraviolet absorption spectra of antibiotic A26201-1 and antibiotic A26201-2 are shown in FIG. 2 and FIG. 3 respectively. A Perkin-Elmer Lamda-3 spectrophotometer (with automatic baseline correction for methyl alcohol absorbance) was used for this determination. The maximum absorptions of the two antibiotics are as follows:

| Solvent | Concentration (weight/volume) | λ max (nanometers) Antibiotic A26201-1 | Antibiotic A26201-2 |
|---|---|---|---|
| 100% methyl alcohol | 0.1% | 205.7, 220.8, 291 (minor), 218 (inflection) | 207.3, 220.5, 273 (minor), 282 (minor), 291.2 (minor), 218 (infection) |
| methyl alcohol with 0.1N hydrochloric acid | 0.1% | 205.3, 220.8, 292 (minor), 218 (inflection) | 204, 220.9, 271.3 (minor), 280.2 (minor), 289.5 (minor), 212.3 (inflection) |
| methyl alcohol with 0.1N sodium hydroxide | 0.1% | 217.4, 292.7 (minor) | 218.6, 280 (minor), 289.3 (minor) |

(C) Infrared Analysis

Figure 4:
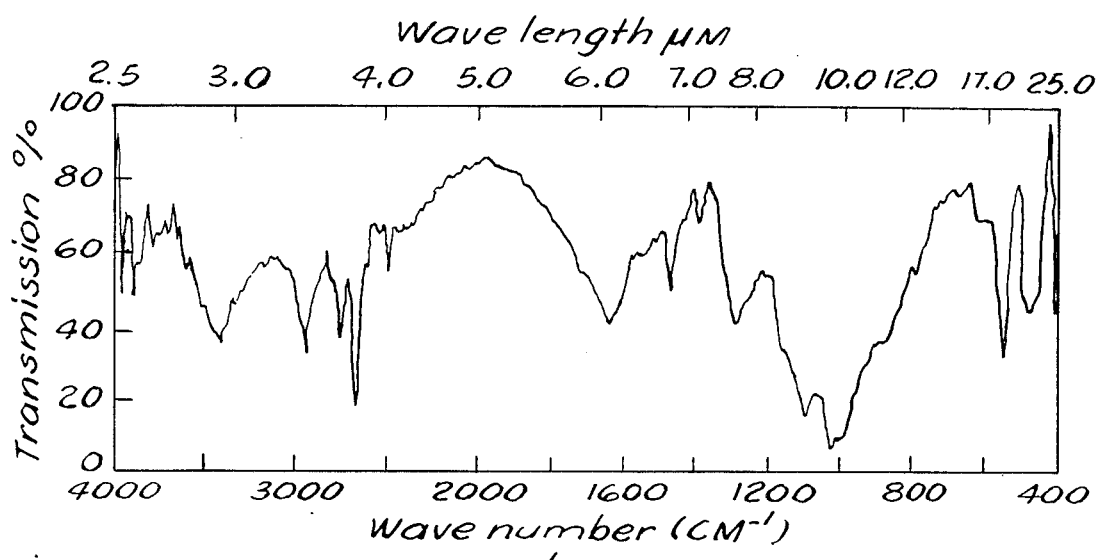
FIG. 4—Infrared absorption spectrum of antibiotic A26201-1.
Figure 5:
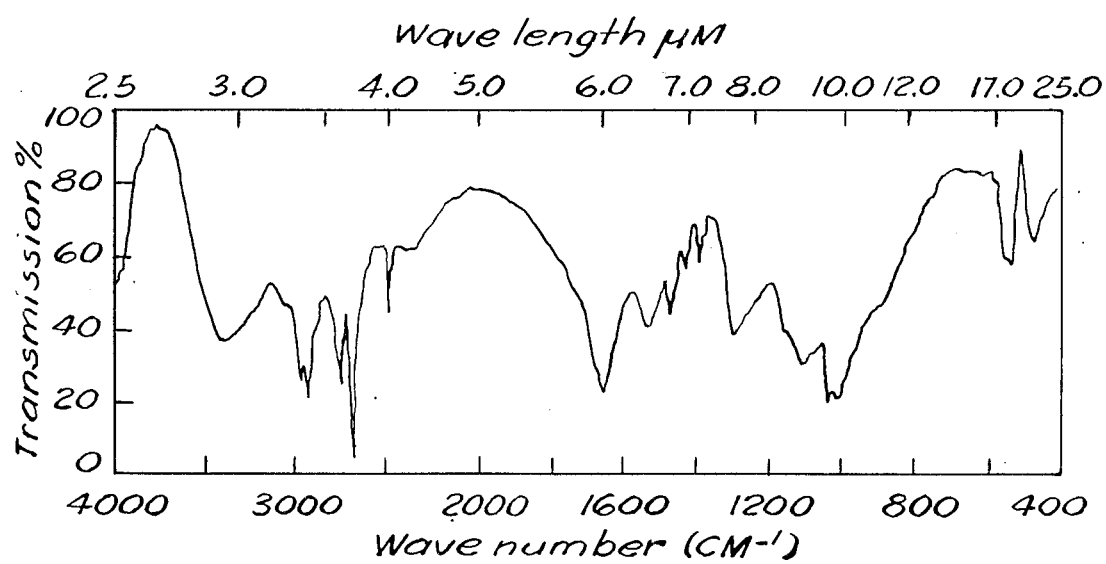
FIG. 5—Infrared absorption spectrum of antibiotic A26201-2.

Antibiotic A26201-1 and antibiotic A26201-2 were subjected to Fourier transform infrared analysis using a KBr pellet. The infrared spectra of antibiotic A26201-1 and antibiotic A26201-2 are shown in FIG. 4 and FIG. 5, respectively, which reveal similarities between the components and indicate peptide characteristics demonstrated by absorption from secondary amide bonds at 1,650 $cm^{-1}$ and 1,520 $cm^{-1}$. A sharp peak occurs at 2,680 $cm^{-1}$ and a split peak is noted at 1,000–1,030 $cm^{-1}$.

(D) Amino Acid and Carbohydrate Analyses

Amino acid analyses of antibiotic A26201-1 and antibiotic A26201-2 revealed the presence of the following amino acids in both components: alanine, cysteine, glutamic acid, glycine, isoleucine, leucine, serine, tryptophan, and valine. All amino acid determinations other than tryptophan involved acid hydrolysis followed by high performance liquid chromatography in accordance with standard procedures known in the art. For the cysteine determination, the samples were oxidized with performic acid prior to acid hydrolysis. For the tryptophan determination, the method of Hugli and Moore, JBC, 247, 2828 (1972), was used which involved an alkaline hydrolysis.

Carbohydrate analyses of both antibiotics ("Phenol Method", Dubois, M, Gilles, K. A., Hamilton, J. K., Rebers, P. A., and Smith, F., Anal. Chem., 28, 350–356, (1956)) indicated the presence of only trace amounts of sugars.

(E) Nuclear Magnetic Resonance (NMR) Analysis

Figure 6:
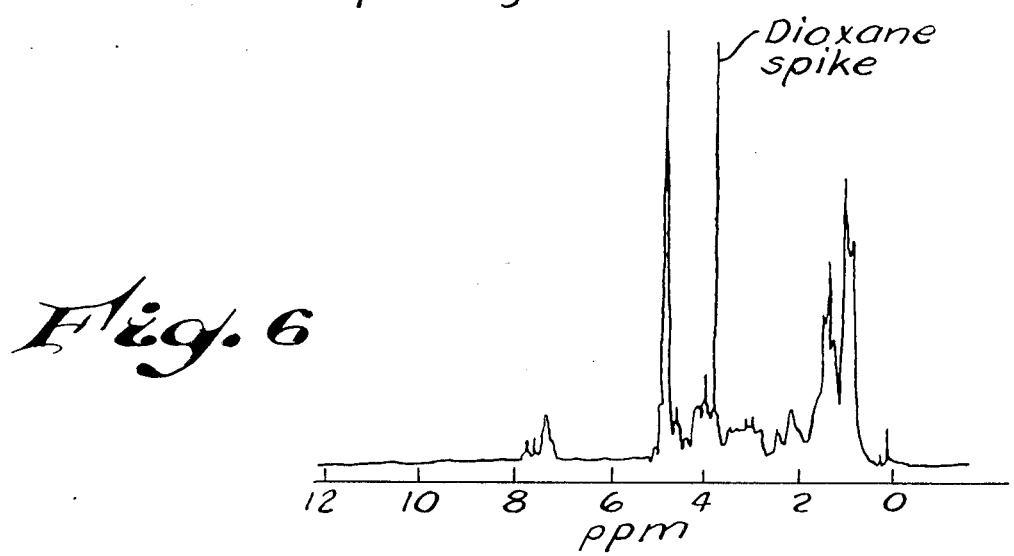
FIG. 6—Proton nuclear magnetic resonance spectrum of antibiotic A26201-1. The spectrum contains a dioxane spike which was included as an internal control.
Figure 7:
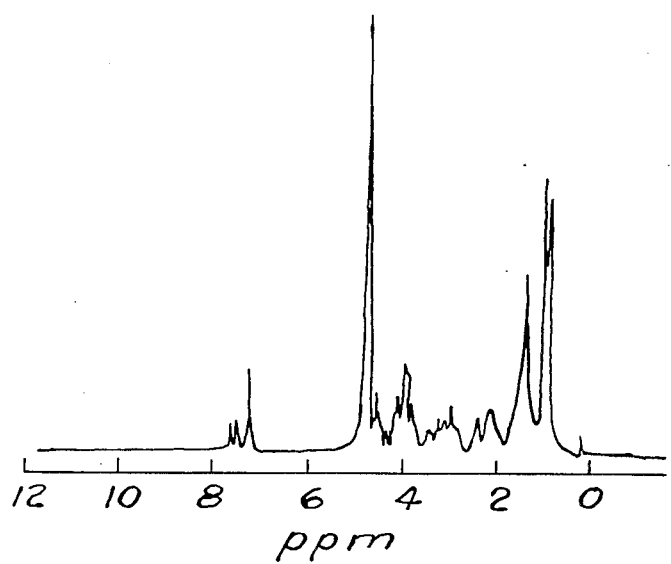
FIG. 7—Proton nuclear magnetic resonance spectrum of antibiotic A26201-2.

Proton NMR analyses were performed on antibiotic A26201-1 and antibiotic A26201-2 in $D_2O$ at 200 ppm the results of which are shown in FIG. 6 and FIG. 7, respectively. Peaks at 2.8–3.3 ppm and 7.2–7.7 ppm can both be attributed to tryptophan. Characteristic peaks are also present at approximately 1.0 ppm, 1.5 ppm, 2.2 ppm, 2.4 ppm, 3.7 ppm, and 4.6 ppm, respectively.

(F) Elemental Analysis

Elemental analyses of antibiotic A26201-1 and antibiotic A26201-2 were performed after drying (48 hours lyophilization at sub-zero temperatures followed by drying in a hot air oven). The results are as follows:

| | Weight % | |
|---|---|---|
| Element | Antibiotic A26201-1 | Antibiotic A26201-2 |
| C* | 33.2 | 45.9 |
| H* | 7.0 | 6.8 |
| N* | 6.7 | 12.0 |
| O** | 51.7 | 29.8 |
| S* | 1.4 | 5.5 |
| Cl*** | Trace | Trace |

*combustion analysis
**by difference (subtraction)
***neutron = activation

From the elemental analysis, simple calculations yield tentative empirical formulae as follows:

| Antibiotic A26201-1 | Antibiotic A26201-2 |
|---|---|
| $C_{55}H_{140}O_{64}N_{10}S$ | $C_{45}H_{80}O_{22}N_{10}S_2$ |

On the basis of the empirical formulae, estimated minimum molecular weights of the two components were determined to be approximately 2000 and 1200, respectively. The relative sulfur analysis is in agreement with the ratio between cysteine residues of the components.

EXAMPLE 6

The biological activities of the novel antibiotics of this invention were determined by various methods as follows:

(A) Antimicrobial Activity

Minimum inhibitory concentrations (MIC's) were determined respectively for the crude broth material, antibiotic A26201, antibiotic A26201-1, antibiotic A26201-2, and gardimycin against a number of different microorganisms. The following techniques were used to determine the MIC's:

Thirty ml aliquots of trypticase soy agar were respectively placed in individual tubes. The agar was melted and then cooled to about 45° to 50° C. A concentration (2-fold serial dilutions of the highest concentration tested) of test antibiotic was added to each individual tube. Each test mixture was stirred and poured into an individual petri plate so that each petri plate contained a single concentration of antibiotic. When the agar hardened, the plates were inoculated with either aerobic or anaerobic test organisms. The plates inoculated with aerobic organisms were incubated at 37° C. for 24 hours and read for bacterial growth. The same plates were again incubated at 30° C. for an additional 48 hours at which point they were checked for yeast and fungal growth. The plates inoculated with anaerobic organisms were incubated at 37° C. in an anaerobic chamber and read at 48 hours. In all cases, the MIC's represent the lowest concentration of antibiotic which demonstrated suppression of growth. The results are summarized in Table 5.

broth material. From this comparision it was determined that the crude broth material promoted the growth of the young chickens.

(C) Ruminant Animal Growth Promotion

The antibiotics of this invention were tested in a 24 hour in vitro ruminant growth promotion system.

A fermentation medium useful for carrying out the evaluations described herein was prepared by the admixture of the following ingredients:

| | |
|---|---|
| Mineral solution 1 | 7.5 ml |
| Mineral solution 2 | 7.5 ml |
| Micromineral solution | 1.5 ml |
| Resazurin solution 0.1% | 0.1 ml |
| Clarified rumen fluid | 10.0 ml |
| $NaHCO_3$ (6.33% solution) | 8.0 ml |
| $Na_2S.9H_2O$ (2.5% solution) | 0.5 ml |
| Distilled water | 64.9 ml |
| | 100.0 ml |

To each 100 ml of the above preparation, 0.8 g of dry nutrients was added. The dry nutrients consisted of 0.3 g of Avicel ® PH 101-microcrystalline cellulose, 0.3 g of casein, and 0.1 g each of anhydrous glucose and soluble starch. The pH of the medium was checked and adjusted to pH 6.8 to 7.2 with $CO_2$.

The clarified rumen fluid of the fermentation medium was prepared by collecting rumen fluid from an untreated fistulated cow on a hay diet approximately 12 hours after feeding. The fluid was strained through gauze and centrifuged at 5,000 rpm. The supernatant was placed in one liter amber bottles (about 400 ml/bottle) and autoclaved at about 15 pounds of pressure for sterilization.

TABLE 5
Minimum Inhibitory Concentration of *Actinoplanes* Antibiotics Against a Number of Microorganisms

| | MIC (μg/ml) | | | | |
|---|---|---|---|---|---|
| Organism | Crude Broth* Material | Antibiotic A26201 | Antibiotic A26201-1 | Antibiotic A26201-2 | Gardimycin |
| *Actinomyces viscosus* | 1250 | 50 | 5.5 | 5.5 | 12.5 |
| *Clostridium perfringens* | 156 | 5 | 2.75 | 2.75 | 3.1 |
| *Clostridium septicum* | 312 | 5 | >11 | 2.75 | 3.1 |
| *Bacteroides fragilis* | >5000 | >50 | >11 | >22 | >50 |
| *Bacteroides multiacidus* | >5000 | >50 | >11 | >22 | >50 |
| *Streptococcus faecalis* | >5000 | >50 | <11 | >22 | 25 |
| *Streptococcus mutans* | >5000 | >50 | >11 | >22 | >75 |
| *Streptococcus bovis* | >5000 | >50 | >11 | >22 | >75 |
| *Lactobacillus casei* | >5000 | >50 | >11 | >22 | >75 |
| *Fusobacterium necrophorum* | >5000 | >50 | >11 | >22 | >75 |
| *Candida albicans* | >5000 | >50 | >11 | >22 | >75 |
| *Aspergillus niger* | >5000 | >50 | >11 | >22 | >75 |
| *Mucor miehei* | >5000 | >50 | >11 | >22 | >75 |
| *Pircularia oryzae* | >5000 | >50 | >11 | >22 | >75 |
| *Bacillus subtilis* | 2500 | >50 | >11 | >22 | 75 |
| *Erwinia amylovora* | 5000 | >50 | >11 | >22 | >75 |
| *Staphylococcus aureus* | 5000 | >50 | >11 | >22 | 75 |
| *Escherchia coli* | >5000 | >50 | >11 | >22 | >75 |
| *Salmonella typhimurium* | >5000 | >50 | >11 | >22 | >75 |
| *Pseudomonas aeruginosa* | >5000 | >50 | >11 | >22 | >75 |
| *Sarcina lutea* | 625 | 50 | 2.75 | 5.5 | 1.5 |

*unaltered aqueous fermentation broth (B) Monogastric Animal Growth Promotion

The crude broth material from the fermentation of Actinoplanes species A26201 was dried onto a portion of standard feed, then the feed containing the broth was mixed with a test diet and fed to young chickens (chicks). The weights of these chicks were compared to the weights of chicks fed a test diet without the crude All of the solutions of the fermentation medium were added as prepared stock solutions of the following compositions (in grams per liter of water):

|  | grams/liter |
|---|---|
| Mineral Solution 1 | |
| $K_2HPO_4$ | 12.5 |
| Mineral Solution 2 | |
| $KH_2PO_4$ | 12.5 |
| $MgSO_4.7H_2O$ | 3.0 |
| NaCl | 12.0 |
| $CaCl_2.2H_2O$ | 1.6 |
| Micromineral Solution | |
| $FeSO_4.7H_2O$ | 0.200 |
| $H_3BO_3$ | 0.030 |
| $CoCl_2.6H_2O$ | 0.020 |
| $ZnSO_4.7H_2O$ | 0.010 |
| $MnCl_2.4H_2O$ | 0.003 |
| $Na_2MoO_4.2H_2O$ | 0.003 |
| $NiCl_2.6H_2O$ | 0.002 |
| $CuCl_2.2H_2O$ | 0.001 |
| (pH adjusted to about 2) | |
| Resazurin Solution 0.1% | |
| Resazurin | 1.0 |
| Sodium Bicarbonate Solution 6.33% | |
| $NaHCO_3$ | 63.3 |
| (saturated with, and stored under 100% $CO_2$) | |
| Sodium Sulfide Solution 2.5% | |
| $Na_2S.9H_2O$ | 25.0 |
| (stored under nitrogen) | |

The in vitro evaluations of antibiotic A26201, antibiotic A26201-1 and antibiotic A26201-2 were carried out in 24 hour batch fermentations in anaerobic digestors having gas and liquid sampling ports and manometers to measure total gas production during the fermentation. Different concentrations of antibiotic A26201 (10, 25, and 100 ppm) as well as antibiotic A26201-1 (2.5, 10, and 50 ppm) and antibiotic A26201-2 (2.5 ppm) were prepared in 10% methanol solutions and placed in separate groups of digestors.

Fresh rumen fluid (700 ml) from an untreated fistulated cow was added to 1300 ml of the fermentation medium previously described, and mixed. After mixing, 10 ml was removed and analyzed as a control, and 200 ml was placed in each of the digestors. The manometers were attached and nitrogen was bubbled through to remove oxygen. The digestors were then maintained at 40° C. while under continuous agitation.

The cultures were sampled at 0, 5 and 24 hours. The 5 hour sample was used primarily to note effects on nitrogen metabolism. Measurement of the change in concentration of protein, amino acids and ammonia in the fermentation after 5 hours was an indication of the extent to which the rate of protein degradation and deamination were inhibited by the antibiotics. Concentrations of isoacids, i.e., iso-butyric, iso-valeric and valeric acids were determined at 24 hours and used as a measure of inhibition of deamination since the major source of these acids is the deamination of the amino acids valine, leucine and proline, respectively.

The 24 hours sample was used to measure volatile fatty acid production. The mole ratio of acetate to propionate (A/P) was used to determine if the antibiotics increased the molar proportion of propionate in total volatile fatty acid concentrations. The gas composition was also determined at 24 hours and the amount of methane produced was noted. The rate at which gas was produced was determined by reading the manometers at 3, 4, and 5 hours to monitor microbial metabolism. The results of the in vitro fermentations are shown in Table 6. The data generally show that antibiotic A26201, antibiotic A26201-1, and antibiotic A26201-2 improved rumen fermentation efficiency as evidenced by a stimulation of propionate production (the main precursor for gluconeogenesis) and inhibition of the less energy efficient acids. The data also show reduced deamination as evidenced by increased amino-N and reduced valerate and other isoacids (for a more complete discussion of rumen metabolism see Church et al. in "Digestive Physiology and Nutrition of Ruminants", Vol. 2, 1971, pp. 622 and 625 incorporated herein by reference).

TABLE 6

Results of Antibiotics in an Artificial Rumen

| | % of Control | | | | | | |
|---|---|---|---|---|---|---|---|
| | Antibiotic A26201 100 ppm | Antibiotic A26201 25 ppm | Antibiotic A26201 10 ppm | Antibiotic A26201-1 50 ppm | Antibiotic A26201-1 10 ppm | Antibiotic A26201-1 2.5 ppm | Antibiotic A26201-2 2.5 ppm |
| $CH_4$ (methane) | 89 | 102 | 111 | 71 | 85 | 89 | 97 |
| Gas Rate (ml/min) | 86 | 91 | 98 | — | 78 | 72 | 64 |
| Amino-N mg/100 ml | 166 | 154 | 148 | 195 | 199 | 132 | 166 |
| Ammonia-N mg/100 ml | 55 | 63 | 70 | 59 | 66 | 92 | 52 |
| Acetate (A) mM | 100 | 86 | 100 | 69 | 78 | 95 | 77 |
| Propionate (P) | 130 | 118 | 118 | 108 | 113 | 107 | 101 |
| Butyrate (B) | 99 | 103 | 124 | 69 | 86 | 112 | 84 |
| Valerate | 18 | 14 | 36 | 15 | 17 | 72 | 41 |
| Total (A + P + B) | 111 | 100 | 109 | 83 | 91 | 101 | 86 |
| A/P | 77 | 73 | 85 | 64 | 69 | 88 | 76 |
| Total Isoacids* | 49 | 58 | 84 | 41 | 50 | 93 | 57 |

*Total Isoacids = Isovalerate + Isobutyrate + Valerate

What is claimed is:

1. Antibiotic A26201-1 having the following characteristics:

(1) Ultraviolet absorption spectrum (FIG. 2):

| Solvent | Concentration (weight/volume) | λ max (nanometers) Antibiotic A26201-1 |
|---|---|---|
| 100% methyl alcohol | 0.1% | 205.7, 220.8, 291 (minor), 218 (inflection) |
| methyl alcohol with 0.1N hydrochloric acid | 0.1% | 205.3, 220.8, 292 (minor), 218 (inflection) |
| methyl alcohol with 0.1N sodium hydroxide | 0.1% | 217.4, 292.7 (minor) |

(2) Infrared spectrum (FIG. 4):
  The most important absorption bands occur at the following frequencies ($cm^{-1}$): 1,650, 1,520, 2,680 (sharp peak) 1,000–1,030 (split peak)

(3) Amino acid analysis:

Presence of alanine, cysteine, glutamic acid, glycine, isoleucine, leucine, serine, tryptophan, and valine (4) Proton NMR analysis (FIG. 6):
Characteristic peaks at (parts per million) 2.8–3.3, 7.2–7.7, 1.0, 1.5, 2.2, 2.4, 3.7 and 4.6

(5) Elemental analysis:

| Element | Weight Percentage |
| --- | --- |
| Carbon | 33.2 |
| Hydrogen | 7.0 |
| Nitrogen | 6.7 |
| Oxygen | 51.7 |
| Sulphur | 1.4 |
| Chlorine | Trace |

(6) An approximate chemical formula based on the elemental analysis of $C_{55}H_{140}O_{64}N_{10}S$ with an approximate molecular weight of 2000.

2. Antibiotic A26201-2 having the following characteristics:

(1) Ultraviolet absorption spectrum (FIG. 3):

| Solvent | Concentration (weight/volume) | λ max (nanometers) Antibiotic A26201-2 |
| --- | --- | --- |
| 100% methyl alcohol | 0.1% | 207.3, 220.5, 273 (minor), 282 (minor), 291.2 (minor), 218 (inflection) |
| methyl alcohol with 0.1N hydrochloric acid | 0.1% | 204, 220.9, 271.3 (minor), 280.2 (minor), 289.5 (minor), 212.3 (inflection) |
| methyl alcohol with 0.1N sodium hydroxide | 0.1% | 218.6, 280 (minor), 289.3 (minor) |

(2) Infrared spectrum (FIG. 5): The most important absorption bands occur at the following frequencies ($cm^{-1}$): 1,650, 1,520, 2,680 (sharp peak), 1,000–1,030 (split peak)

(3) Amino acid analysis:
Presence of alanine, cysteine, glutamic acid, glycine, isoleucine, leucine, serine, tryptophan and valine (4) Proton NMR analysis (FIG. 7):
Characteristic peaks at (parts per million) 2.8–3.3, 7.2–7.7, 1.0, 1.5, 2.2, 2.4, 3.7 and 4.6

(5) Elemental analysis:

| Element | Weight Percentage |
| --- | --- |
| Carbon | 45.9 |
| Hydrogen | 6.8 |
| Nitrogen | 12.0 |
| Oxygen | 29.8 |
| Sulphur | 5.5 |
| Chlorine | Trace |

(6) An approximate chemical formula based on the elemental analysis of $C_{45}H_{80}O_{22}N_{10}S_2$ with an approximate molecular weight of 1200.

3. A process for producing antibiotic A26201-1 as defined in claim 1 or antibiotic A26201-2 as defined in claim 2 which comprises cultivating under aerobic conditions Actinoplanes species A26201 or a mutant thereof in a suitable culture medium containing a carbon source and a nitrogen source at a pH of about 6 to 8 and at a temperature of about 20° C. to 35° C. until a sufficient amount of either or both of the antibiotics are produced by said microorganism in said culture medium.

4. The process of claim 3 wherein said culture medium includes one of the group consisting essentially of fructose, sucrose, tryptophan or valine.

5. A process for inhibiting bacteria which comprises applying to said bacteria or habitat thereof an effective antibacterial amount of antibiotic A26201-1 as defined in claim 1 or antibiotic A26201-2 as defined in claim 2.

6. The process of claim 5 wherein said bacteria are gram positive bacteria.

7. A process for promoting the growth of animals which comprises administering to said animals an effective growth promoting amount of antibiotic A26201-1 as defined in claim 1 or antibiotic A26201-2 as defined in claim 2.

8. The process of claim 7 wherein said animals are monogastric animals.

9. The process of claim 7 wherein said animals are ruminant animals.

10. An animal feed composition for promoting the growth of animals which comprises a mixture of standard animal feed and an effective growth promoting amount of antibiotic A26201-1 as defined in claim 1 or antibiotic A26201-2 as defined in claim 2.

11. The composition of claim 10 wherein said standard animal feed is standard animal feed for monogastric animals.

12. The composition of claim 10 wherein said standard animal feed is standard animal feed for ruminant animals.

13. The animal feed composition of claim 11 wherein the concentration of said antibiotic or antibiotics is about 5 to about 25 parts per million of the ultimate feed composition.

14. The animal feed composition of claim 12 wherein the concentration of said antibiotic or antibiotics is about 2 to about 25 parts per million of the ultimate feed composition.

15. A process for obtaining separate substances, antibiotic A26201-1 as defined in claim 1, and antibiotic A26201-2 as defined in claim 2 which comprises cultivating under aerobic conditions Actinoplanes species A26201 (ATCC 39573) in a suitable culture medium containing a carbon source and a nitrogen source at a pH of about 6 to 8 and at a temperature of about 20° C. to 35° C. until a sufficient amount of either or both of the antibiotics are produced by said microorganism in said culture medium, recovering the crude fermentation broth containing antibiotics, partially purifying the antibiotics by use of a preparative reverse phase liquid chromatography system, and resolving the two antibiotics by use of a semi-preparative high performance liquid chromatography system.

* * * * *